United States Patent [19]  [11]  4,360,526
Zeeh et al.  [45]  Nov. 23, 1982

[54] AZOLYL-ACETOPHENONE-OXIME ETHERS

[75] Inventors: Bernd Zeeh, Ludwigshafen; Ernst-Heinrich Pommer, Limburgerhof; Ernst Buschmann, Ludwigshafen, all of Fed. Rep. of Germany

[73] Assignee: BASF Aktiengesellschaft, Fed. Rep. of Germany

[21] Appl. No.: 905,761

[22] Filed: May 15, 1978

[30] Foreign Application Priority Data

May 27, 1977 [DE] Fed. Rep. of Germany ....... 2723942

[51] Int. Cl.$^3$ .................... A01N 43/64; A01N 43/74; C07D 249/08; C07D 413/12
[52] U.S. Cl. .................................. 424/269; 424/245; 424/272; 424/273 R; 548/101; 548/262; 548/247; 548/341
[58] Field of Search ............... 260/308 R, 307 H, 299; 548/341, 262, 101, 247; 424/245, 269, 273, 272

[56] References Cited

U.S. PATENT DOCUMENTS 3,478,039 11/1969 Bell ....................................... 548/341
4,124,767 11/1978 Mixich et al. ...................... 548/341
4,264,772 4/1981 Kramer et al. ..................... 424/269
4,309,434 1/1982 Kramer et al. ..................... 548/262

FOREIGN PATENT DOCUMENTS 2610022 9/1976 Fed. Rep. of Germany ... 260/308 R
1464224 2/1977 United Kingdom ............ 260/308 R

OTHER PUBLICATIONS

Horsfall, Fungicides and their Action, (Waltham, Mass., 1945), p. 139.

Primary Examiner—Alton D. Rollins
Attorney, Agent, or Firm—Keil & Witherspoon

[57] ABSTRACT

Novel valuable azolyl-acetophenone-oxime ethers and their salts and metal complexes which possess a good fungicidal activity, as well as fungicides which contain these compounds as active ingredients, and processes for combating fungi with these compounds.

10 Claims, No Drawings

AZOLYL-ACETOPHENONE-OXIME ETHERS

The present invention relates to new valuable azolyl-acetophenone-oxime ethers, processes for their preparation and their use as fungicides.

The use of triazolyl-acetophenone derivatives as fungicides has been disclosed (German Laid-Open Application DOS No. 2,431,407). However, their action is unsatisfactory in the case of a variety of fungi.

We have found that new azolyl-acetophenone-oxime ethers of the formula

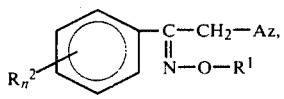

where $R^1$ is alkyl of 1 to 4 carbon atoms, alkenyl, alkynyl of 3 or 4 carbon atoms or cycloalkyl or is aralkyl which is unsubstituted or monosubstituted or polysubstituted by halogen (F, Cl or Br) or trifluoromethyl in the aryl radical, or is heteroarylalkyl, $R^2$ is hydrogen or halogen (F, Cl or Br), n is 1, 2 or 3 and Az is imidazoyl or 1,2,4-triazolyl, and their salts and metal complexes possess a good fungicidal activity which is superior to that of the above conventional fungicides.

Further, we have found that the new azolyl-acetophenone-oxime ethers are obtained when an azolyl-acetophenone of the formula

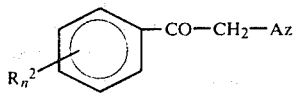

where $R^2$, n and Az have the above meanings, is reacted with hydroxylamine to give the corresponding azolyl-acetophenone-oxime, which is then reacted with a halogen derivative of the formula $$R^1-X$$

where $R^1$ has the above meanings and X is halogen (F, Cl, Br or I). Dialkyl sulfates are a further preferred reactant for carrying out the etherification with alkyl radicals (i.e. if $R^1$ is alkyl). A further possible method of preparation is to react azolyl-acetophenones with O-substituted hydroxylamines of the general formula $$H_2N-O-R^1$$

where $R^1$ has the above meanings.

Because of the C=N double bond, the azolyl-acetophenone-oxime ethers are in the form of geometrical isomers (syn/anti forms) and, as free bases, are often of an oily consistency. They can be characterized by converting them into their salts or metal complex salts, which are in most cases crystalline and also possess excellent fungicidal properties.

The salts can be prepared by reacting the azolyl-acetophenoneoxime ether with an acid (for example hydrochloric acid, nitric acid, sulfuric acid or a carboxylic acid) and the metal complexes can be prepared by reacting the azolyl-acetophenone-oxime ether with a water-soluble inorganic metal salt (for example a copper salt, zinc salt or tin salt).

The azolyl-acetophenones required as starting materials are known from German Laid-Open Applications DOS Nos. 2,431,407 and 2,610,022.

The Examples which follow illustrate the methods of preparation.

EXAMPLE 1

(a) 2,4-Dichloro-ω-(1,2,4-triazol-1-yl)-acetophenone-oxime 10.4 parts by weight of hydroxylamine hydrochloride and 10.6 parts of sodium acetate are dissolved in 100 parts of water. 25.6 parts of 2,4-dichloro-ω-(1,2,4-triazol-1-yl)-acetophenone in 250 parts of ethanol are added and the mixture is refluxed for 2 hours. It is then cooled to 0° C. and the precipitate is filtered off, washed with water and dried. 16 parts of 2,4-dichloro-ω-(1,2,4-triazolyl-1-yl)-acetophenone-oxime of melting point 197° C. are obtained.

(b) 3.12 parts of sodium hydride are added to 200 parts of absolute tetrahydrofuran under a stream of nitrogen. 27.2 parts of 2,4-dichloro-ω-(1,2,4-triazol-1-yl)-acetophenone-oxime (dissolved in 80 parts of dimethylformamide) are added dropwise at 50°-60° C. and the mixture is then refluxed for 2 hours. Thereafter 23.5 parts of 2,4-dichlorobenzyl chloride are added dropwise at 50°-60° C. and the mixture is refluxed for a further 2 hours. 280 parts of water are then added dropwise, the mixture is extracted three times with 100 parts of ether and the organic phases are dried with sodium sulfate. Hydrogen chloride gas is then introduced until the mixture is saturated and the precipitate is filtered off and recrystallized from acetonitrile. 16 parts of 2,4-dichloro-ω-(1,2,4-triazol-1-yl)acetophenone-oxime O-(2,4-dichlorobenzyl) ether are obtained as the hydrochloride, of melting point 173° C.

EXAMPLE 2

6 parts of 2,4-dichloro-ω-(1,2,4-triazol-1-yl)-acetophenone-oxime O-(2,4-dichlorobenzyl) ether are dissolved in 10 parts of ethanol and 2.2 parts of copper-II chloride dihydrate in 7 parts of ethanol (i.e. a saturated solution of the copper salt) are added dropwise at 70° . The mixture is then concentrated under reduced pressure and the solid residue is stirred with ether and filtered off. 4 parts of a copper chloride complex of 2,4-dichloro-ω-(1,2,4-triazol-1-yl)-acetophenone-oxime O-(2,4-dichlorobenzyl) ether, having a decomposition point of 142°-143° C., are obtained; the complex is olive green.

The compounds listed in the Table which follows can be prepared by similar methods.

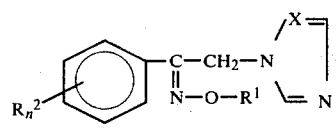

| No. | $R_n^2$ | $R^1$ | Salt/Complex Salt | X | Melting point (°C.) |
|---|---|---|---|---|---|
| 1 | 2,4-Cl | 2,4-dichlorobenzyl | HCl | N | 173 |
| 2 | 2,4-Cl | CH₃ | HCl | N | 141 |
| 3 | 2,4-Cl | C₂H₅ | HCl | N | 159 |
| 4 | 2,4-Cl | allyl | HNO₃ | N | 115+ |
| 5 | 2,4-Cl | propargyl | HNO₃ | N | 108+ |

-continued

Structure: R$_n^2$-phenyl-C(=N-O-R$^1$)-CH$_2$-N(azole where X=CH or N)

| No. | R$_n^2$ | R$^1$ | Salt/Complex Salt | X | Melting point (°C.) |
|---|---|---|---|---|---|
| 6 | 4-Cl | CH$_2$-(3,4-dichlorophenyl) | HCl | CH | 127 |
| 7 | 4-Br | CH$_3$ | HCl | N | 157–159 |
| 8 | 4-Br | CH$_2$-(4-chlorophenyl) | HCl | N | 167–169 |
| 9 | 4-Br | CH$_2$-(3,4-dichlorophenyl) | HCl | N | 168–170 |
| 10 | 4-Br | CH$_2$-(4-chlorophenyl) | ½ CuCl$_2$ | N | 182–184[1] |
| 11 | 4-Br | CH$_2$-(3,4-dichlorophenyl) | ½ CuCl$_2$ | N | 171[1] |
| 12 | 4-Cl | CH$_3$ | HCl | N | 156–158 |
| 13 | 4-Cl | CH$_2$-(3,4-dichlorophenyl) | — | N | 91 |
| 14 | 4-Cl | CH$_3$ | ½ CuCl$_2$ | N | 207[1] |
| 15 | 4-Cl | CH$_2$-(3,4-dichlorophenyl) | ½ CuCl$_2$ | N | 158–160[1] |
| 16 | 2,4-Cl | CH$_2$-(4-chlorophenyl) | HCl | N | |
| 17 | 2,4-Cl | CH$_2$-(2-chlorophenyl) | HCl | N | |
| 18 | 2,4-Cl | CH$_2$-(2,4-dichlorophenyl) | HCl | N | |
| 19 | 2,4-Cl | CH$_2$-(2,4-dichlorophenyl) | CuCl$_2$ | N | 142–143[1] |
| 20 | 2,4-Cl | CH$_2$-(5-ethylisoxazol-4-yl) | — | N | oil[2] |
| 21 | 2,4-Cl | CH$_2$-(4-fluorophenyl) | — | N | oil[2] |
| 22 | 2,4-Cl | CH$_2$-(3-methylisoxazol-4-yl) | — | N | oil[2] |
| 23 | 2,4-Cl | CH$_2$-(5-chloro-3-methylisoxazol-4-yl) | — | N | oil[2] |
| 24 | 2,4-Cl | CH$_2$-C≡CH | CuCl$_2$ | N | 152[1] |

+with decomposition
[1]with decomposition
[2]characterized by the NMR spectrum

The azolyl-acetophenone-oxime ethers of the invention are distinguished by excellent activity against a broad spectrum of phytopathogenic fungi. Some of them exert a systemic action and can be used as foliar fungicides and soil fungicides and especially as a seed dressing.

The new compounds are in particular suitable for combating the following plant diseases: *Erysiphe graminis* (powdery mildew) in cereals, *Erysiphe cichoriacearum* (powdery mildew) in Cucurbitaceae, *Podosphaera leucotricha* in apples, *Uncinula necator* in grapes, *Erysiphe polygoni* in beans, *Sphaerotheca pannosa* in roses, *Puccinia* species in cereals and *Uromyces* species in beans.

The compounds are applied by spraying or dusting the plants with the active ingredients or treating the seeds of the plants with the active ingredients. They may be applied before or after infection of the plants or seeds by the fungi.

The compounds of the invention can be converted into the conventional formulations, e.g. solutions, emulsions, suspensions, dusts, powders, pastes and granules. The form in which the compound is applied depends entirely on the end use but should in every case ensure fine uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzenes, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95 percent by weight of active ingredient, preferably from 0.5 to 90 percent.

The formulations, and the ready-to-use preparations obtained therefrom, e.g. solutions, emulsions, suspensions, powders, dusts, pastes or granules, are applied in the conventional manner, e.g. by spraying, atomizing, dusting, scattering or watering.

The amounts used depend on the nature of the desired effect and are from 0.01 to 3, but preferably from 0.01 to 1, kg of active ingredient per hectare.

The above ready-to-use preparations may contain other active ingredients together with those according to the invention, e.g. herbicides, insecticides, growth regulators and other fungicides or may be mixed with fertilizers and applied together with these. When the active ingredients are mixed with other fungicides, the fungicidal spectrum of action is in many cases broadened.

The list of fungicides given below, with which the compounds according to the invention can be combined, is intended to illustrate the possible combinations, but the invention is in no way limited to these.

Examples of fungicides which can be combined with the metal complexes of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc, N,N-ethylene-bis-dithiocarbamate and N,N'-polyethylene-bis(thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazolecarbamate, 2-methoxycarbonylamino-benzimidazole, 2-thiocyanatomethylthio-benzthiazole, 4-(2-chlorophenyl-hydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethyl-furan-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts and 2,6-dimethyl-N-cyclododecyl-morpholine and its salts.

For the experiments which follow, the conventional active ingredients shown below were used for comparative purposes:

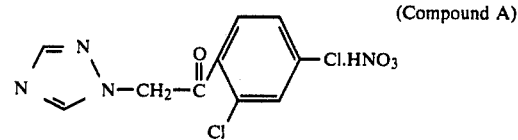

(Compound A)

Known from German Laid-Open Application DOS No. 2,431,407.

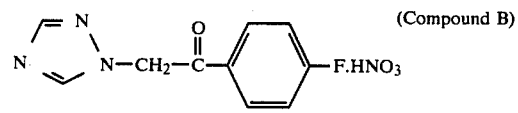

(Compound B)

Known from German Laid-Open Application DOS No. 2,431,407.

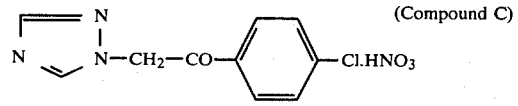

(Compound C)

Known from German Laid-Open Application DOS No. 2,431,407.

EXAMPLE 3

Action on Barley Mildew

Leaves of pot-grown barley seedlings are sprayed with an aqueous emulsion of 80% by weight of active ingredient and 20% of emulsifier and, when the spray coating has dried, the leaves are dusted with oidiae (spores) of barley mildew (*Erysiphe graminis* var. *hordei*). The test plants are then set up in a greenhouse at from 20° to 22° C. and from 75 to 80% relative atmospheric humidity. After 10 days, the degree of development of the mildew fungi is determined.

| Active ingredient | Infection of the leaves after spraying with a liquor containing ... % of active ingredient | | |
|---|---|---|---|
| | 0.05 | 0.025 | 0.012 |
| 2 | 0 | 0 | 0 |
| 3 | 0 | 0 | 0 |
| 4 | 0 | 0 | 0 |
| 5 | 0 | 0 | 0 |
| A } conventional | 0 | 2 | 2 |
| B } fungicides | 3 | 5 | 5 |
| Untreated (control) | 5 | 5 | 5 |

0 = no infection, graded to 5 = total infection

EXAMPLE 4

Action on Leaf Rust of Wheat

Leaves of pot-grown wheat seedlings of the "Caribo" variety are dusted with spores of leaf rust (*Puccinia recondita*). The pots are then placed in a high humidity (90–95%) chamber at from 20° to 22° C. for 24 hours.

During this time, the spores germinate and the germ tubes penetrate into the leaf tissue. The infected plants are then sprayed to run-off with aqueous liquors of 0.05, 0.025 and 0.012% strength by weight, the solids comprising 80% of active ingredient and 20% of ligninsulfonate. After the spray coating has dried, the test plants are set up in a greenhouse at from 20° to 22° C. and from 65 to 70% relative humidity. After 8 days, the degree of development of the rust fungi on the leaves is determined.

| Active ingredient | Infection of the leaves after spraying with a liquor containing . . . % of active ingredient | | |
|---|---|---|---|
| | 0.05 | 0.025 | 0.012 |
| 2 | 0 | 0 | 0 |
| 3 | 0 | 0 | 0 |
| 4 | 0 | 0 | 0 |
| 5 | 0 | 0 | 0 |
| C conventional fungicide | 5 | 5 | 5 |
| Untreated (control) | 5 | 5 | 5 |

0 = no infection, graded to 5 = total infection

EXAMPLE 5

Action on Crown Rust of Oats

Using the method described in Example 3, leaves of pot-grown oat seedlings of the "Flämings Krone" variety are dusted with spores of crown rust of oats (*Puccinia coronata*) and placed in a high humidity chamber. The infected plants are then sprayed to runoff with an 0.05% strength by weight aqueous spray liquor in which the solids comprise 80% of active ingredient and 20% of ligninsulfonate. After the leaves have dried, the pots are placed in a greenhouse at from 20° to 22° C. and from 65 to 70% relative humidity. After 8 days, the degree of development of the rust fungi on the leaves is determined.

| Active ingredient | Infection of the leaves after spraying with a liquor containing 0.05% of active ingredient |
|---|---|
| 2 | 0 |
| 3 | 0 |
| 4 | 0 |
| 5 | 0 |
| 1 | 0 |
| A } conventional fungicide | 2 |
| B | 0 |
| C | 0 |
| Untreated (control) | 5 |

EXAMPLE 6

Action on Barley Mildew

Use as a Seed Dressing 100 g samples of barley seed, "Asse" variety, are carefully treated for about 5 minutes, in glass bottles, with 300 mg (=0.3% by weight) of the dressings shown in the Table. Groups of 8 grains are then placed in pots and covered with soil. 10 days after the barely has emerged, the leaves are dusted with oidia (conidia) of barley mildew (*Erysiphe graminis* var. *hordei*). The test plants are then set up in a greenhouse at from 20° to 22° C. and 75 to 80% relative humidity. After a further 10 days, the degree of development of the powdery mildew fungi on the leaves is determined.

| Active ingredient | . . . % of active ingredient in the dressing | Degree of mildew infection of the leaves 10 days after artificial infection |
|---|---|---|
| 2 | 40 | 0 |
| 4 | 40 | 0 |
| 5 | 40 | 0 |
| A | 40 | 1–2 |
| B } conventional fungicide | 40 | 5 |
| C | 40 | 5 |
| Untreated (control) | | |

0 = no infection, graded to 5 = total infection

EXAMPLE 7

90 parts by weight of Compound 1 are mixed with 10 parts by weight of N-methyl-α-pyrrolidone and a solution suitable for use in the form of very fine droplets is obtained.

EXAMPLE 8

20 parts by weight of Compound 2 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of calcium dodecylbenzenesulfonate and 5 parts by weight of the adduct of 40 moles of ethylene oxide with 1 mole of castor oil. On pouring the solution into 100,000 parts by weight of water and finely distributing it therein, an aqueous dispersion containing 0.02 percent by weight of the active ingredient is obtained.

EXAMPLE 9

20 parts by weight of Compound 3 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. On pouring the solution into 100,000 parts by weight of water and finely distributing it therein, an aqueous dispersion containing 0.02 percent by weight of the active ingredient is obtained.

EXAMPLE 10

20 parts by weight of Compound 1 are dissolved in a mixture which consists of 25 parts by weight of cyclohexanol, 65 parts by weight of a mineral oil fraction of boiling range 210°–280° C. and 10 parts by weight of the adduct of 40 moles of ethylene oxide with 1 mole of castor oil. On pouring the solution into 100,000 parts by weight of water and finely distributing it therein, an aqueous dispersion containing 0.02 percent by weight of the active ingredient is obtained.

EXAMPLE 11

20 parts by weight of active ingredient 2 are thoroughly mixed with 3 parts by weight of sodium diisobutylnaphthalene-α-sulfonate, 17 parts by weight of the sodium salt of a ligninsulfonic acid obtained from a sulfite waste liquor and 60 parts by weight of silica gel powder, and the mixture is milled in a hammer mill. On finely dispersing the mixture in 20,000 parts by weight of water, a spray liquor containing 0.1 percent by weight of active ingredient is obtained.

EXAMPLE 12

3 parts by weight of Compound 3 are intimately mixed with 97 parts by weight of finely divided kaolin. A dusting agent containing 3 percent by weight of the active ingredient is thus obtained.

EXAMPLE 13

30 parts by weight of Compound 4 are intimately mixed with a mixture of 92 parts by weight of silica gel powder and 8 parts by weight of paraffin oil which has been sprayed on the surface of this silica gel. The resulting formulation of the active ingredient adheres well.

EXAMPLE 14

40 parts by weight of active ingredient 1 are intimately mixed with 10 parts of the sodium salt of a phenolsulfonic acid/urea/formaldehyde condensate, 2 parts of silica gel and 48 parts of water. A stable aqueous dispersion is obtained. This can be diluted with 100,000 parts by weight of water to give an aqueous dispersion containing 0.04 percent by weight of active ingredient.

EXAMPLE 15

20 parts of active ingredient 2 are intimately mixed with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

We claim:

1. An azolyl-acetophenone-oxime ether of the formula

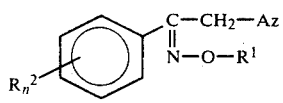

where $R^1$ is alkyl of 1 to 4 carbon atoms, alkenyl of 3 to 4 carbon atoms, alkynyl of 3 to 4 carbon atoms, phenyl, benzyl, benzyl mono- or polysubstituted in the phenyl ring with F, Cl, Br or Cf$_3$, dr $R^1$ is the group

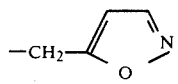

wherein the isoxazole ring can be substituted with methyl, ethyl, or halogen, $R^2$ is hydrogen or halogen, n is 1, 2 or 3 and Az is 1,2,4-triazolyl, and its salts and metal complexes.

2. A process for combating fungi, wherein the areas in which fungi are to be completed are treated with an effective amount of an azolylacetophenone-oxime ether of the formula

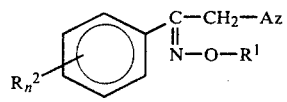

where $R^1$ is alkyl of 1 to 4 carbon atoms, alkenyl of 3 to 4 carbon atoms, alkynyl of 3 to 4 carbon atoms, phenyl, benzyl, benzyl mono- or polysubstituted in the phenyl ring with F, Cl, Br or CF$_3$, or $R^1$ is the group

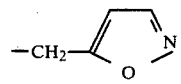

wherein the isoxazole ring can be substituted with methyl, ethyl, or halogen, $R^2$ is hydrogen or halogen, n is 1, 2 or 3 and Az is 1,2,4-triazolyl, or a salt or metal complex thereof.

3. A triazole derivative selected from the group consisting of 2,4-dichloro-ω-(1,2,4-triazol-1-yl)-acetophenone-oxime O-(2,4-dichlorobenzyl) ether hydrochloride, 2,4-dichloro-ω-(1,2,4-triazol-1-yl)-acetophenone-oxime O-ethyl ether hydrochloride, 2,4-dichloro-ω-(1,2,4-triazol-1-yl)-acetophenone-oxime O-allyl ether nitrate, 2,4-dichloro-ω-(1,2,4-triazol-1-yl)-acetophenone-oxime O-propargyl ether nitrate and 2,4-dichloro-ω-(1,2,4-triazol-1-yl)-acetophenone-oxime O-methyl ether hydrochloride.

4. An ether as defined in claim 1 wherein $R^1$ is alkyl of 1 to 4 carbon atoms, alkenyl or alkynyl of 3 or 4 carbon atoms, or benzyl which is unsubstituted or monosubstituted or polysubstituted by halogen or trifluoromethyl in the phenyl radical.

5. An ether as defined in claim 1 wherein $R^1$ is one of the $R^1$ substituents set forth in the Table in Example 2 of the specification.

6. A process as defined in claim 2 wherein $R^1$ of said ether is alkyl of 1 to 4 carbon atoms, alkenyl or alkynyl of 3 or 4 carbon atoms, or benzyl which is unsubstituted or monosubstituted or polysubstituted by halogen or trifluoromethyl in the phenyl radical.

7. A process as defined in claim 2 wherein $R^1$ of said ether is one of the $R^1$ substituents set forth in the Table in Example 2 of the specification.

8. A fungicidal composition comprising an effective amount of ether as defined in claim 1 and a solvent or carrier therefor.

9. A fungicidal composition comprising an effective amount of ether as defined in claim 4 and a solvent or carrier therefor.

10. A fungicidal composition comprising an effective amount of ether as defined in claim 5 and a solvent or carrier therefor.

* * * * *

UNITED STATES PATENT AND TRADEMARK OFFICE
CERTIFICATE OF CORRECTION

PATENT NO. : 4,360,526

DATED : November 23, 1982

INVENTOR(S) : Bernd Zeeh, Ernst-Heinrich Pommer et al

It is certified that error appears in the above-identified patent and that said Letters Patent is hereby corrected as shown below:

Column 9, line 46, "$Cf_3$" should read -- $CF_3$ --.

Column 9, line 46, "dr" should read -- or --.

Column 9, line 58, "completed" should read -- combated --.

Signed and Sealed this

Seventh Day of June 1983

[SEAL]

Attest:

DONALD J. QUIGG

Attesting Officer

Acting Commissioner of Patents and Trademarks